United States Patent [19]
Goix

[11] Patent Number: 5,798,222
[45] Date of Patent: Aug. 25, 1998

[54] APPARATUS FOR MONITORING SUBSTANCES IN ORGANISMS

[75] Inventor: Philippe J. Goix, Oakland, Calif.

[73] Assignee: Guava Technologies, Inc., Oakland, Calif.

[21] Appl. No.: 503,095

[22] Filed: Jul. 17, 1995

[51] Int. Cl.$^6$ .............................. C12Q 1/02; C12Q 1/00; C12Q 1/22; C12Q 1/04

[52] U.S. Cl. .............................. 435/29; 435/4; 435/31; 435/34; 435/287.1; 435/283.1; 435/808; 435/968; 422/82.01; 422/82.08

[58] Field of Search .............................. 435/29, 31, 34, 435/4, 292.1, 283.1, 287, 808, 968, 288.7, 287.1; 422/50, 82.01, 82.08; 372/9

[56] References Cited

U.S. PATENT DOCUMENTS

| | | | |
|---|---|---|---|
| 4,354,114 | 10/1982 | Karnaukhov et al. | 422/50 |
| 4,392,236 | 7/1983 | Sandstrom et al. | 435/288.7 |
| 4,500,641 | 2/1985 | van den Engh et al. | 435/292.1 |
| 4,521,512 | 6/1985 | Silman | 435/29 |
| 4,723,511 | 2/1988 | Solman et al. | 422/50 |
| 4,753,878 | 6/1988 | Silman | 435/29 |
| 5,089,416 | 2/1992 | Schwartz et al. | 436/8 |
| 5,093,866 | 3/1992 | Douglas-Hamilton et al. | 382/6 |
| 5,094,944 | 3/1992 | Hayes | 435/29 |
| 5,324,940 | 6/1994 | Ekstrom | 422/50 |
| 5,380,663 | 1/1995 | Schwartz et al. | 436/10 |

FOREIGN PATENT DOCUMENTS

| | | | |
|---|---|---|---|
| 0 045 623 | 2/1982 | European Pat. Off. | G01N 33/18 |

OTHER PUBLICATIONS

JuChelka, et al., "Rapid Toxicity Assessment Using Ingestion Rate of Cladocerans and Ciliates." Archives of Environmental Contamination and Toxicology, vol. 28, pp. 508–512 (1995).

Burbank, et al., "Rapid Toxicity Assessment Using Esterase Biomarkers in *Brachionus calyciflorus* (Rotifera)." Environmental Toxicology and Water Quality: An International Journal, vol. 9 (1994) pp. 171–178.

Juchelka, et al., "Rapid Toxicity Assessment Using Rotifer Ingestion Rate," Arch. Environ. Contam. Toxicol. vol. 26, pp. 549–554 (1994).

A.L. Ooms–Wilms, et al., "Clearance Rates of Bacteria by the Rotifer *Filinia iongiseti* (Ehrb.) measured using three tracers," Hydrobiologia, vols. 255/256, pp. 255–260 (1993).

Snell, et al., "Biomarkers for Managing Water Resources," Technical Completion Report, USDI/USGS Project G. 1556(03), Agreement No. 14–08–001–1556, Apr. 1993.

Walford, et al., "Replacing Live Foods with Microencapsulated Diets in the Rearing of Seabass (*Lates calcarifer*) Larvae: Do the Larvae Ingest and Digest Protein–Membrane Microcapsules?," Aquaculture, vol. 92, pp. 225–235 (1991).

Kszos, et al., "Effort–Allocation Analysis of the Seven–Day Fathead Minnow (*Pimephales promelas*) and *Ceriodaphnia Dubia* Toxicity Tests," Env. Toxicological Chemistry 10, 68–72 (1991).

*Primary Examiner*—Louise N. Leary
*Attorney, Agent, or Firm*—Wilson Sonsini Goodrich & Rosati

[57] ABSTRACT

An apparatus for monitoring a substance in a living organism. The apparatus can be used to provide an assessment of the feeding rate of the organism and can be used to measure water toxicity.

14 Claims, 6 Drawing Sheets

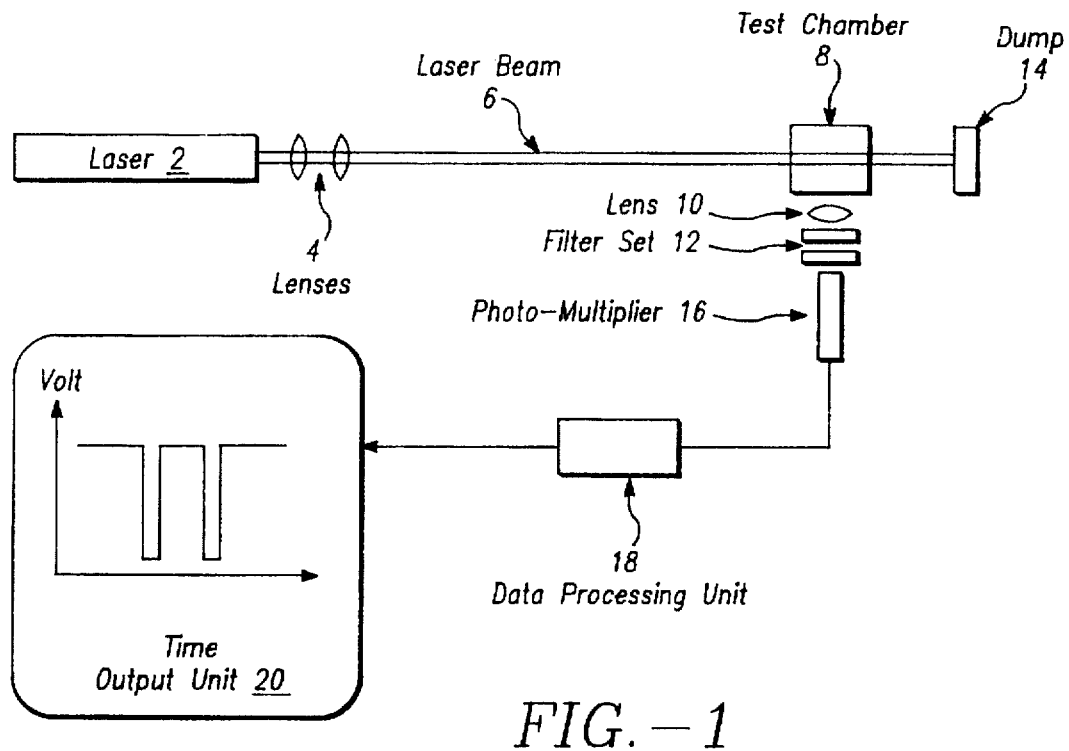
FIG. -1
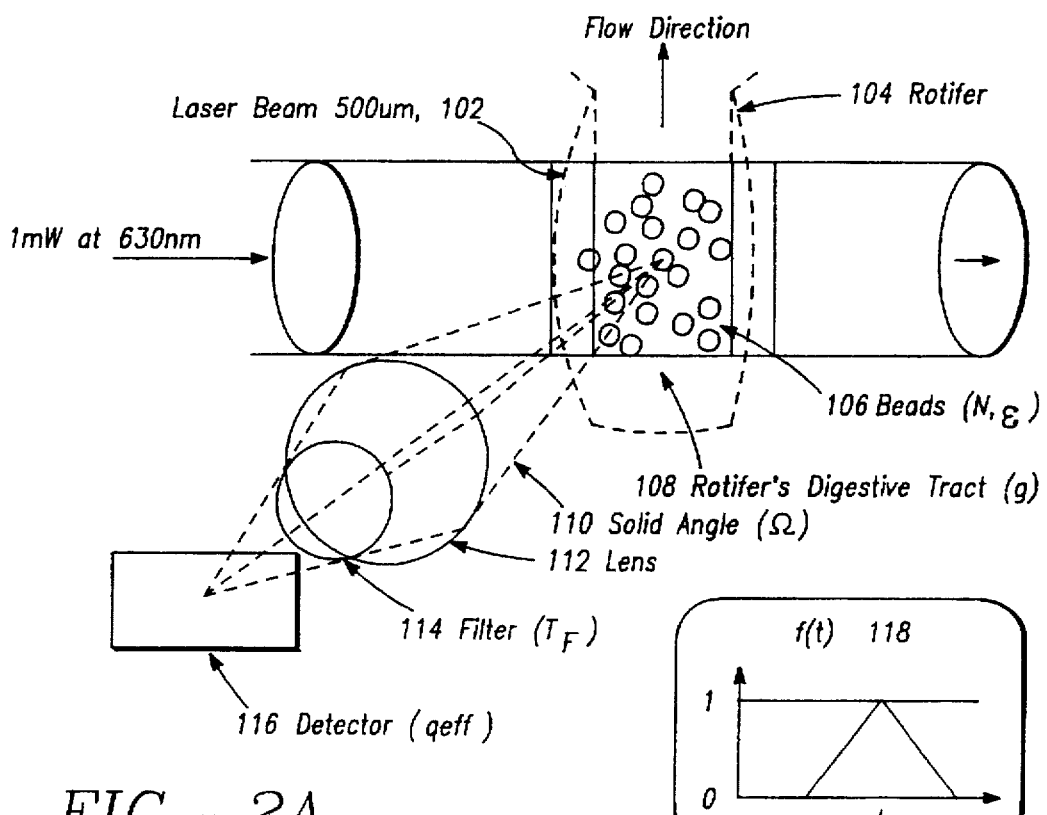
FIG. -2A
FIG. -2B

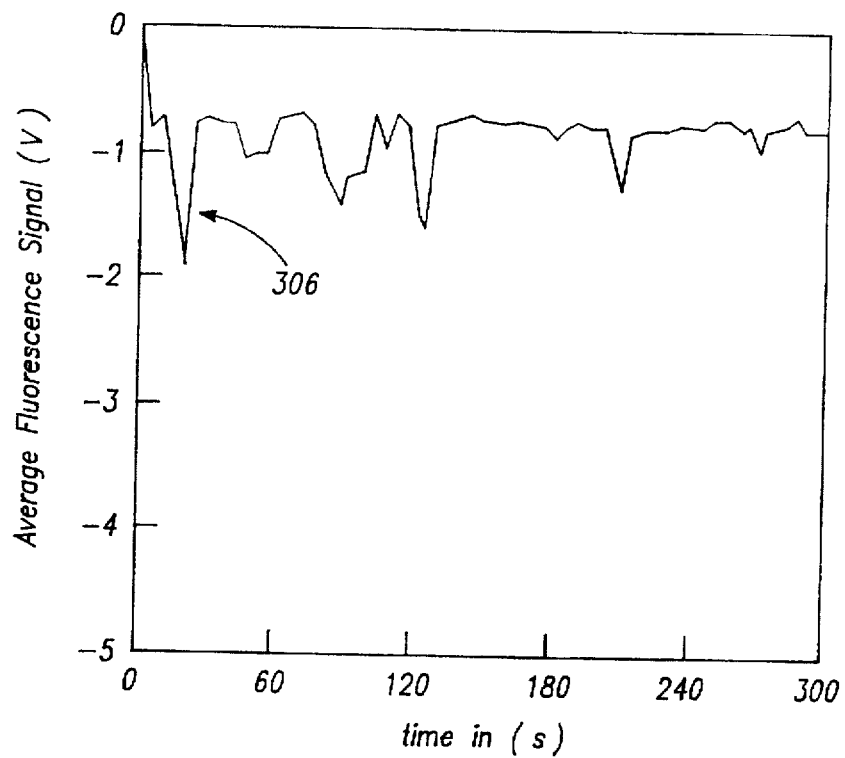
FIG.—4B
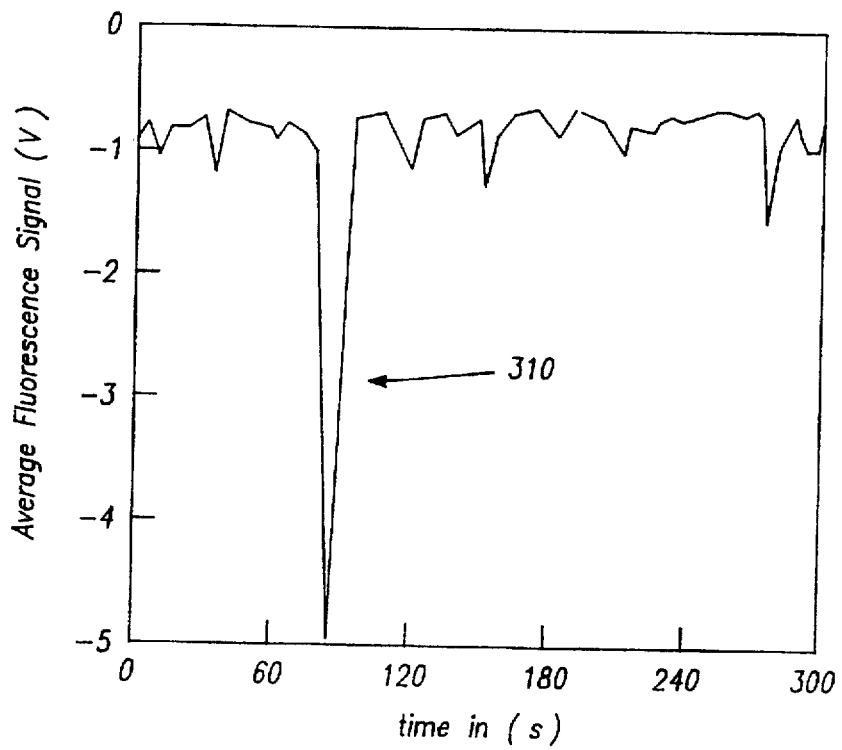
FIG.—4C

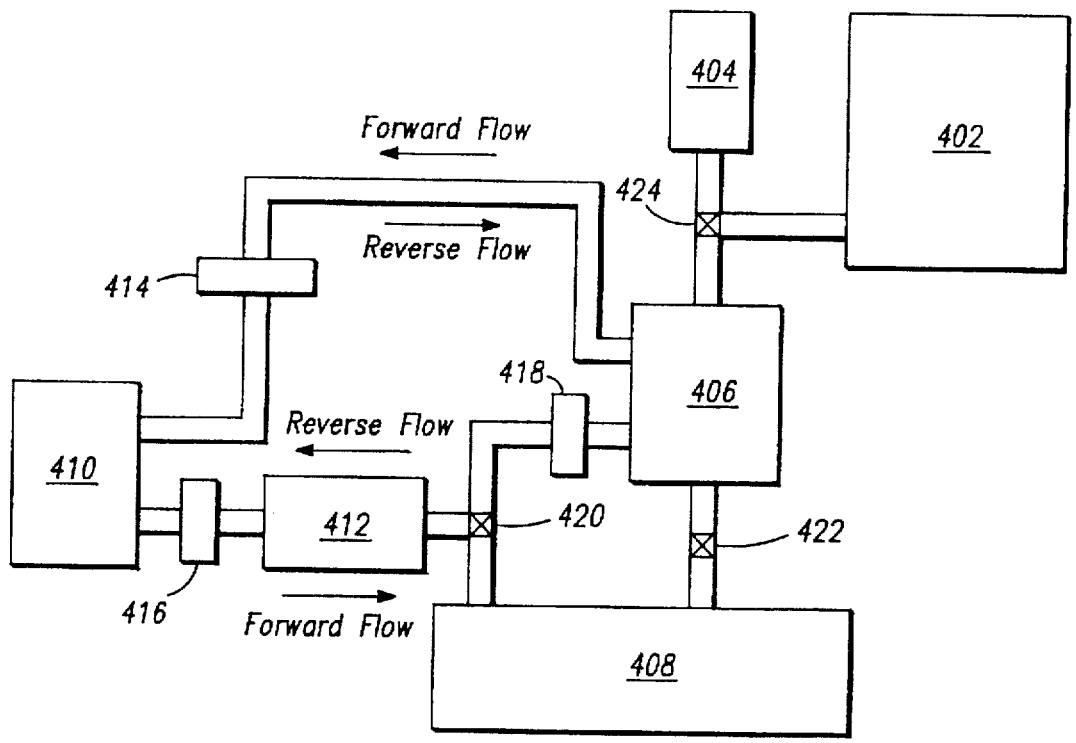
FIG.—5A
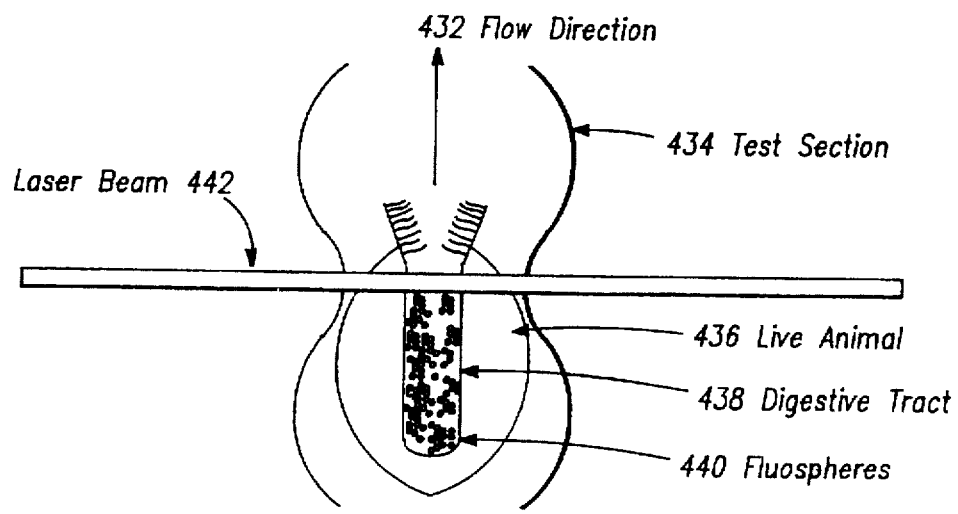
FIG.—5B

APPARATUS FOR MONITORING SUBSTANCES IN ORGANISMS

FIELD OF INVENTION

The present invention relates to the use of electromagnetic radiation to monitor a biological function of a living organism and, more particularly, to the use of light to monitor the feeding rate of living organisms to assess the toxicity or the quality of water.

BACKGROUND OF THE INVENTION

Fresh water is a scarce resource on earth. While water represents 71% of the earth's surface area with an estimated volume of 100 quadrillions of gallons, 97% of this amount is salt water, 2% is ice water, and the rest of the water is divided in lakes, rivers, water ways and ground water. (Jacques Sironneau, "L'eau Resource Stratégique", Ministére de l'Environment, Géopolitique, Automne 1993, No 43, pp. 45–69). The relatively small proportion of fresh water on earth is indicated by the following example: if the total water supply of the earth were represented by a gallon, only a tea spoon would represent fresh water. Although fresh water is very limited, its demand is continuously increasing due to demographic and economic forces. The recent worldwide drought cycle of 1989–1991 has highlighted the importance of water. Therefore, water quality monitoring is vital to sustain the economical growth of developed and developing countries.

Environmental contamination caused by human activities is a widespread problem causing serious economic consequences in various ecosystems. Water, air, and soil have been contaminated by a variety of products resulting from human activities. For example, chemical insecticides used in the California Central Valley orchards contaminate surface water in that region. Analysis of surface waters in the San Joaquin Valley has shown acute toxicity to invertebrates used in water toxicity tests. (Foe, C., and R. Sheipline. "Pesticides in Surface Water from Applications on Orchards and Alfalfa During the Winter and Spring of 1991–92." Regional water quality control board central Valley Region report p. 79, February, 1993).

Water way contamination in Georgia is an example of the magnitude of the water contamination problem. Of the 71,143 stream miles in Georgia, only 3,635 have been sampled. Of those tested, 2,899 miles (80%) were determined to be too contaminated to be fishable or swimmable (Snell, T. D. Dusenberry, L. Dunn, and N. Walls, "Biomarkers for Managing Water Resources.", Georgia Institute of Technology, p. 43, 1993)

Because of the health and ecological threats posed by water contamination, water monitoring is vital. The magnitude of this issue is highlighted by the water situation in Northern California. The San Francisco Bay-Delta watershed system provides drinking water for 20 million people (⅔ of the state). Every year, 7 million acre feet of water are diverted from this ecosystem through aqueducts (1 acre feet=325,900 gallons).

The current standard methods to ascertain toxicity of effluents use three organisms as indicators of water toxicity: the fathead minnow, *Pimephales promelas*; the cladoceran, *Ceriodaphnia dubia*; and the green alga, *Selenastrum capricornutum*. These organisms are cultured under standard conditions and selected stages are exposed for various periods of time to graded series of toxicants. Survival and reproduction of the test organisms exposed to the toxicants provides an indication of water toxicity (EPA. "Short Term Methods for Estimating Chronic Toxicity of Effluents and Receiving Water to Freshwater Microorganisms." Third edition, Environmental Monitoring and Support Laboratory, Cincinnati, Ohio, EPA/600/4-85/014, 1985).

These methods have serious shortcomings: they are slow, cumbersome and exhibit variability between laboratories. For example, for six samples, five ambient samples plus a control or five concentrations of an effluent plus a control, the larval survival and growth test of *P. promelas* takes seven days. The *D. dubia* survival and reproduction tests also takes seven days. All the tasks required for these tests require a total of 53.6 person hours (Lynn, Adams K., and A. J. Stewart. "Effort—Allocation Analysis of the Seven-Day Fathead Minnow (Pimephales Promelas) and Ceriodaphnia Dubia Toxicity Tests", Environ. Toxicol. Chem., Vol. 10, .pp.: 67–72, 1991).

The variation in results when different laboratories conduct these tests is shown in several research papers (Degrave, G. M., and Cooney, J. D. "Ceriodaphania. An Update on Effluent Toxicity Testing and Research Needs", Environ. Toxicol. Chem. Vol. 6, pp. 331–333, 1987), (Buikema A. L. "A Variation in Static Acute Toxicity Tests Results With *Daphnia magna* Exposed to Refinery Effluents and Referenced Toxicants. Oil. Petroleum Pollut. Vol. 1, pp. 189–198, 1983), (Grothe, D. R., and Kimerle, R. A. "Inter and Intralaboratory Variability in *Daphnia magna* Effluent Toxicity Tests Results." Environ. Toxicol. Chem, Vol. 4, p. 192, 1985), ("Donn, P. B., and Rodgers, J. R., "Variability Associated With Identification of Toxic in National Pollutant and Discharge Elimination System, NPDES, Effluent Toxicity Tests." Environ. Toxicol. Chem. Vol. 8, 893–902, 1989).

Because of the limitations mentioned above, new rapid, sensitive, reproducible and inexpensive tests to assess water toxicity are needed. These methods would help industry to comply with government regulations on amounts of toxic chemicals permitted in discharges and would assist government agencies, such as the EPA, to enforce more stringent regulations and to efficiently monitor water quality.

The "Microtox test" was developed to address these needs. Microtox is the first biosensor designed to assess the toxicity of water using a bioluminescent bacteria. The "Microtox test" offers several advantages because it can provide, under certain conditions, a measure of toxicity in less than one hour. The Microtox test is based on the use of a suspension of luminescent microorganisms. When toxic samples inhibit the metabolic process of these microorganisms, their light output decreases in proportion to this inhibition. However, since Microtox uses bacteria, it does not provide the same ecological information as methods using plants and animals. Bacteria do not have the ecological and physiological complexity necessary to reflect the effects of toxic substances on all components of ecosystems. Recent studies published by Aqua Survey have shown that the "Microtox test" is significantly less sensitive to many chemicals found in treated municipal waste waters than the EPA-approved procedures (Hayes, K. R. "Fluorescent Aquatic Bioassay and Procedures", U.S. Pat. No. 5,094, 944, 1992).

Another variation of the methods using bacteria to assess water toxicity utilizes a specially designed enzyme substrate that becomes fluorescent when cleaved. This substrate is cleaved by enzymes in bacteria and emits fluorescent light when exposed to light of the proper wave length. The rate of enzyme activity can be measured using a fluorometer, and provides an indirect measurement of the level of toxicant stress on the organisms. In this method, a number of living organisms are placed in an aquatic sample containing an enzyme substrate present at sufficient concentration to allow an enzymatic modification of the substrate to produce a detectable fluorescence signal. If enzyme activity is depressed, it is concluded that the water contains a certain toxicant level (Hayes, K. R. 1992 loc. cit.).

Many researchers have suggested that zooplankton feeding behavior has a useful endpoint in the study of toxicity in aquatic ecosystem. Juchelka and Snell have recently performed extensive work to develop rapid methods to assess aquatic toxicity (C. M. Juchelka, T. W. Snell, "Rapid Toxicity Assessment Using Rotifer Ingestion Rate," Archives of Environmental Contamination and Toxicology, Vol. 26, pp. 549–554, 1994. C. M. Juchelka, T. W. Snell, "Rapid Toxicity Assessment Using Ingestion Rate of Cladocerans and Ciliates," Archives of Environmental Contamination and Toxicology, Vol. 28, pp. 508–512, 1995). In particular, in these studies, the feeding behavior of the rotifer *Brachionus calyciflorus*, for fresh water, and the rotifer *Brachionus plicatilis* for marine waters has been studied, as an endpoint of aquatic toxicity for a wide range of chemicals. Systematically, and, for identical conditions, the results have been compared to current *Ceriodaphnia dubia* reproduction methods, the acute methods, and to the Microtox test. According to Juchelka and Snell's recent findings (C. M. Juchelka, T. W. Snell, 1995 loc. cit), the rotifer feeding rate method correlates very well with the Ceriodaphnia EPA approved current method for a wide range of chemicals.

In Snell's method, rotifers are exposed for several minutes to water containing a toxicant; then they are allowed to feed on fluorescent labeled 2 µm beads for 5 minutes. They are then anesthetized, washed, and transferred to a microscope slide and examined individually using a fluorescent microscope. The ingestion rate is estimated by quantifying the intensity of fluorescence of ingested beads in the digestive tract of individual rotifers using an imaging technique (Snell et. al, 1993, loc. cit). More recently Juchelka and Snell (Juchelka and Snell loc. cit. 1995) successfully used the same experimental protocol on various aquatic invertebrates such as *C. dubia* and the marine rotifer *B. plicatilis*. The study showed that for rotifers and *C. dubia*, the feeding rate protocol compared very well with the toxicity tests based on reproduction endpoints.

Snell's method however has the following shortcomings inherent to the fluorescent device and method used to assess the toxicity: First, the device is too labor intensive because it requires the transfer of individual rotifers after they are exposed to the toxicant and the fluorescent beads, and it requires visual examination through the microscope to continuously monitor individual rotifers. Second, the device lacks precision. The dynamic range of a camera and digital imaging system is significantly smaller (or more expensive for equal performance) than a single point photo detector connected to a classical 12 bit analog digital converter. In this study, the fluorescence coming from the beads ( 2µm in Snell study) was measured with a 25% precision (2.8 ±0.72) fluorescence unit per bead (Snell et. al loc. cit., p. 14, 1993).

The methodology is not favorable for large sample statistics. Only 15 samples were used for statistical analysis. This reduces the precision, the reliability and the reproducibility of the method.

In summary, this method is a cumbersome, expensive, multi-step biological assays (exposure of rotifers, selection of individual rotifers, anesthetizing of rotifers, individual examination and imaging of rotifers). Therefore, this technique is not applicable for extensive toxicity monitoring as required for the assessment and remediation of many environmental sites.

Among the methods currently available to assess the toxicity of aquatic ecosystems, none are automatic. In fact, most of them are labor intensive, capital extensive and costly. The fluorescence based methods measuring biological response of various organisms also are in this category. As previously discussed, the feeding rate method proposed by Snell is still cumbersome, non-automatic and labor intensive because it is a multi-step test procedure (exposure of rotifers, selection of individual rotifers, anesthetizing of rotifers, individual examination and imaging of rotifers). It is also quite expensive since it requires a fluorescent microscope coupled with a complex imaging systems. However, this method provides a genuine means to assess aquatic toxicity by measuring an ecologically important process since ingestion is essential to many of the components of ecosystems.

Accordingly, there is a need for an apparatus and method for monitoring substances in organisms that address the disadvantages described above and improve on the prior art.

SUMMARY OF THE INVENTION

The present invention encompasses an apparatus and a method for monitoring a substance in individual living organisms. The apparatus and method can be used to provide an assessment of the feeding rate of the organism and can be used to measure water toxicity.

One type of preferred embodiment of an apparatus according to the present invention includes a coherent source of light tuned onto the absorption band of the substance to be monitored, an appropriate set of filters to differentiate the fluorescence light from the coherent incident light, a detector, a carrier flow generator to drive the living organism to be monitored into a transparent probe volume section where the light measurements are performed, and a signal and data processing system to convert, transform and analyze the signal into a substance concentration measurement.

A preferred embodiment of a method to analyze water samples according to the present invention includes the steps of exposing the living organisms for a time period to a toxic and a non-toxic (reference) sample, exposing the living organisms to a fluorescent substance, washing the exposed organisms to remove external fluorescent particles, transporting and orienting individual living organisms to the probe volume section, detecting automatically the characteristic signal corresponding to the presence of an exposed organisms, processing the fluorescence of the exposed organisms to both the non-toxic and the toxic samples, performing statistical analysis for both toxic and non-toxic sample, comparing the process feeding rate values in both samples to deduce the toxicity level of the analyze sample.

The many advantages of the present invention will become clear to those skilled in the art from the present disclosure. Among many other advantages, the present invention offers the following advantages over existing methods:

The present invention provides the end user with an analytical tool to analyze biological responses of complex organisms.

The present invention is automatic, as opposed to labor intensive.

The present invention provides the end-user with a faster response than many existing technologies.

The present invention is less expensive than existing technologies.

The present invention is relatively reliable, because it can use larger statistical samples than existing EPA approved bioassay methods.

The present invention is relatively versatile, because the instrument can be adapted to a wide range of living organisms, such as, but not limited to, rotifers *Brachionus calyciflorus* for fresh waters, and *Brachionus plicatilis* for marine waters.

Because the present invention is automatic, it can be used for continuous monitoring.

Because the present invention is automatic, it reduces human error in the ecological assessment.

The present invention also allows for embodiments that are light and battery powered, thereby allowing for on-site toxicity measurement.

By measuring stress in individual organism, the present invention can provide a genuine way to measure toxicity concentration as defined by EPA's methods.

Among other reasons, the present invention is advantageous because it integrates state-of-the-art aquatic toxicology with state-of-the-art of laser, detection, signal and data processing as well as a flow-carrier system designed specially designed for, but not limited to, rotifers and Ceriodaphnia.

Among other advantages, the present invention offers advantages over conventional epifluorescent microscope and imaging systems since it provides a time trace of a fluorescent signal which can be detected from the controlled passage of a living organism through the laser probe volume section rather than a fluorescent picture which will need to be analyzed by a trained operator.

Among other reasons, the present invention is also advantageous because it specifically addresses the different processes associated with measuring fluorescent substances inside the digestive tract of a living animals in a consistent, reproducible, and automatic fashion.

Among other advantages, the present invention offers advantages over conventional fluorometers because it measures fluorescent substances inside individual living organisms automatically and performs statistical analysis from a series of these individual measurements, rather than measuring the average fluorescence signal inside a chamber.

Among other advantages, the present invention is advantageous over conventional flow-cytometers because the flow system of proposed instrumentation device is adapted to, and capable of being specifically designed to, address the incubation and washing steps inherent to the feeding rate methods. In some embodiments, the test section where the fluorescence measurement on live animals occurs is specifically designed for rotifers and Ceriodaphnia, the flow velocity control system takes into account the motility of the animals, and the acquisition and data processing software is specifically designed to provide the feeding rate data and other parameters associated with these measurements.

BRIEF DESCRIPTION OF THE DRAWINGS

FIG. 1 shows an embodiment of the present invention

FIGS. 2(a) and 2(b) show a detailed diagram of the probe section.

FIG. 4(b) shows a display of the detector output when rotifers cross the probe volume and have ingested crimson fluosphere during 20 minutes prior to the measurement.

FIG. 4(c) shows a display of the detector output when rotifers cross the probe volume and have ingested crimson fluosphere during 45 minutes prior to the measurement.

FIG. 5(a) shows a preferred display of a carrier flow generator, the feeding and washing processes inherent to a feeding rate measurement by fluospheres.

FIG. 5(b) shows a preferred display of a probe volume section.

DETAILED DESCRIPTION OF THE INVENTION

Figure 3:
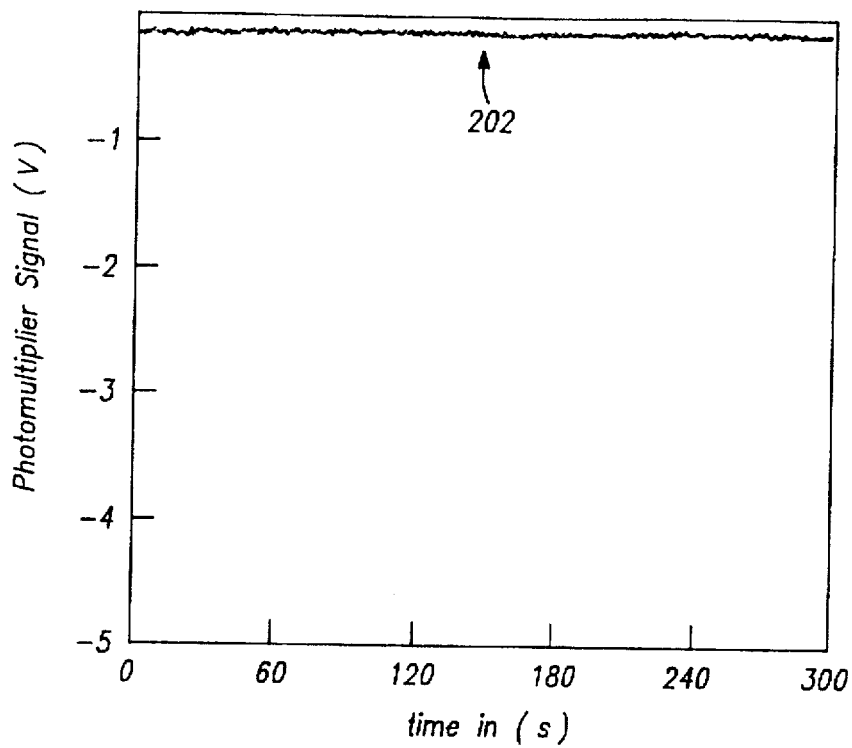
FIG. 3 shows a display of the detector output when rotifer cross the probe volume in absence of fluosphere. This signal is usually referred as background signal.

A preferred embodiment of the present invention provides a mechanism to quantify substances inside living organisms. More specifically, by using fluorescent beads as a marker and quantifying their concentration in the digestive tract of individual living organisms, an apparatus according to the present invention allows a measurement of the feeding rate of these organisms and hence provides an assessment of their toxic stress when exposed to various water samples.

An embodiment of an apparatus according to the present invention is shown in the four following figures: FIG. 1, FIG. 2 (which includes both FIG. 2(a) and FIG. 2(b), (FIG. 5(a) and FIG. 5(b).

FIG. 1 shows a preferred embodiment of the fluorescence single point device. A source of light 2 generates a laser beam 6. Using a set of lenses 4, the laser beam 6 is focused onto a transparent test chamber 8. A light dump 14 is placed on the other side of the test chamber to collect the laser light. A photo-multiplier 16 is placed at a 90 degree angle of the laser beam, imaging the focused laser beam 6 across the test chamber 8 using the lens 10. A filter set 12 is placed before the photo-multiplier to isolate fluorescence light from ambient and laser beam light. A data processing unit 18 is connected to the photo-multiplier to process the timed photo-multiplier output 20. The photomultiplier output 20 is characterized by a voltage signal 22 delivered by the dector and represented on the vertical axis, in volt, versus time 21 represented on the horizontal axis. The peak 23, viewed by the detector, represents the passage across the laser beam of an individual living organism containing fluorescent beads in its digestive tract. When the voltage intensity of this peak is greater than a set threshold, the peak is recognized by the system as a measure. The signal processing includes a measure of the photo-multiplier background signal and a threshold analysis to recognize the presence of a fluorescence peak.

As shown in FIG. 1, representing a view from above of the apparatus, to best operate the detector 16, the filter set 12, and the lens 10 should be all positioned perpendicularly to the laser beam 6. The test chamber 8, is shown as a square. The set of filters 12 placed before the detector 16 is designed to block the non-absorbed laser light and to transmit the fluorescence light generated by the laser light absorption process.

FIG. 2 represents a frontal view of a more detailed embodiment of a portion of the apparatus to monitor substances in organisms. The laser beam 102 is, in this case, 500 μm and has a light power output of 1 mw at the wavelength of 630 nm; it is directed across the living organism, in this case the rotifer 104. The rotifer 104 has ingested the beads 106. The beads 106 are present in the rotifer's digestive tract 108, in number N and have a constant light absorption coefficient ε at the laser wave length. The rotifers are flowing across the laser beam 102, in this case from the bottom to the top of the drawing into the test chamber 120. The lens 112 is imaging the rotifer digestive tract 108 when crossing the laser beam 102 with a solid angle Ω 110, onto the photodetector 116 of a quantum efficiency qeff. A filter 114 with an optimum transmittance TF at the maximum fluorescence wavelength and maximum blockage at all other wavelengths is placed before the detector 116. The function f(t) 118 represents a simplified time-convolution between the laser beam light distribution 102 and the passage of the rotifer digestive tract 108 across the imaged beam. The detector 116, the filter 114, and the imaging lens 112 are all placed perpendicularly to the laser propagating beam direction FIG. 5(a) represents a detailed embodiment of a preferred carrier flow device. This device is comprised of 5 tanks 402, 404, 406, 408, and 410. A reverse peristaltic pump 412. A test section 414 where the fluorescence measurement are performed. Two filters 416 and 418. Three 3 way valves 420, 422, 424. The preferred flow carrier system, depicted on (FIG. 5a), performs the organism incubation process with beads, the washing process and the fluorescence measurements. The living organisms are placed in the tank 406. A solution of fluorescent beads is placed in the tank 404. The valve 424 is positioned to allow the content of the tank 404 to flow into the tank 406. After a 5 minute incubation process the pump 412 is set on forward position, the valve 420 is set to allow the flow through the tank 408. The valve 422 is closed. Under this conditions the organisms are flowing through the test chamber 414 and are carried into the tank 410 from the tank 406. While the water containing the beads is flushed through the filter 416 the organisms, in this case the rotifers, are retained in the tank 410 by the water filter 416. The larger tank 402 supplies the system with fresh water during the washing process. Since the washing water is flowing through the test section 414 an assessment of the number beads still contained in the water can be made by making a signal background measurement. When the fluorescence signal is lower than a set threshold, the washing process is completed. Then the pump 412 is set on the reverse direction, and the valve 420 connects the filter 418 to the pump 412. The tank 408 is isolated from the system and the rotifer in the tank 410 are flowing through the test section 414 in a controlled fashion where the fluorescent measurements can be made.

FIG. 5(b) details a preferred embodiment for the test section. The live animal, in this case the rotifer, 436, is composed of a digestive tract 438, in which the fluosphere or beads 440 are present. Due the embodiment described in (FIG. 5a), the live animal 436 and its digestive tract 438 are moving across the laser beam 442 along the flow direction 432. In this case, the test section 434 is designed to force the digestive tract of the live animal 436 to flow through perpendicularly to the laser beam 442.

To avoid trajectory ambiguity in measurements and in order to ensure the digestive tract 438 is oriented with respect to the laser bear 442 in a constant fashion, the test section 434 can be designed specifically for a given live animal. For example, in some embodiments, an oblong animal is transported through a tube having a cross-section that is larger than the smallest cross-section of the animal, but smaller than the largest cross-section of the animal, so that the animal's digestive tract is oriented perpendicular to the laser beam, as shown in FIG. 5(b). It will be recognized by those skilled in the art, based on the present disclosure, that a wide variety of methods of orienting an animal may be used with the present invention and such methods are also within the scope of the present invention. It will further be recognized that the present invention does not absolutely require such orientation, and that embodiments of the invention exist wherein there are no means for orienting the animal.

As shown on FIG. 5(b), the live animal 436 is oriented properly in the test section 434 when its digestive tract 438, describe as, but not limited to, a rectangle is oriented perpendicularly to the laser beam 432. By moving along the flow direction 432, at a controlled speed, the total amount of fluospheres contained into the digestive tract 438 will be illuminated consistently by the laser beam.

The invention can utilize a single point light detection device based on fluorescence technique. The general fluorescence technique is a powerful technique widely used in a variety of fields for more than 30 years and is therefore well-known to those of ordinary skill in such fields. The tremendous improvements of the light source technologies, such as continuous lasers, pulsed lasers as well as diode lasers; detector technologies, such as cameras or single point photo detectors; filters technologies, such as interference filters; and dye technologies, such as fluorescent beads have expanded the applications of this powerful technique. The relation between the fluorescence intensity and the concentration of a fluorescent dye can be expressed as followed (George G. Guilbault, Practical Fluorescence, 2nd Edition, 1990):

$$I_F = \phi * I_0 (1 - e^{-b*\epsilon*c}) \quad (1)$$

Where, $I_0$ is the incident light intensity, $I_F$ is the fluorescence light intensity, ε is the molar absorptivity of the dye, b is the path length of the probe volume, c is the concentration of the dye, and φ is the fluorescence efficiency of the dye. In this invention, the dye is contained in the fluosphere. We want to measure the concentration of the beads contained in the rotifers' digestive tract. Equation (1) could then be rewritten as follows:

$$I_F = \phi * I_0 (1 - e^{-g*\epsilon_b*n_b}) \quad (2)$$

Where g is the size of the rotifer digestive tract, $\epsilon_b$ is the absorptivity of one bead, and nb is the bead concentration per unit length. When $g*\epsilon_b*n_b$ is small, typically lower than 0.05, then the fluorescence signal becomes proportional to the concentration of the dye. The concentration of dye contained in the fluosphere is kept small enough to remain in a fluorescence regime called a linear regime:

$$I_F = \phi * I_0 * g * \epsilon_b * n_b \quad (3)$$

According to the experimental set up shown on (FIG. 1), the fluorescence signal is derived from a narrow band laser source tuned onto the absorption spectrum of a fluorescent dye contained in the latex bead. A set of filters is blocking all radiation but the fluorescence signal.

The fluorescent signal recorded onto a photo detector is converted and electronically amplified to an output voltage signal. This output signal, proportional to the fluorescence signal, is digitized and stored on a computer for further data processing. By using this technique, the amount of fluorescent beads ingested by individual living organisms can be tagged by the laser. The narrow wavelength band width of the laser (few manometers), the fluorescence efficiency, $\phi$, of the dye, ($\phi$=0.92 for the fluoreceine, $\phi$=0.97 for the rhodamine, George G. Guilbault, Practical Fluorescence, 1st Edition, 1973), the size and the concentration of the bead chosen to assess the feeding rate, the sensitivity of the detector, the sample size chosen to statistically represent the living organism population all contribute to optimize the method. The fluorescence peaks corresponding to the number of beads ingested by each rotifer are converted into feeding rate values using a calibration table. This calibration table is, in effect, specific to the device. Once each fluorescence value is converted into a feeding rate value, a statistical analysis is performed, where distributions, and mean and fluctuating values are compared with a library of referenced (non-toxic) values. By monitoring the departure of these values, from the reference values an estimation of the toxicity can be made.

The use of the apparatus described above will now be set forth in more detail.

As described on FIG. 1, 2, 5(a) and (b) during a toxicity test, with our method, an individual living organism experiences the following steps:

(a) Incubation and feeding steps: The living organism is first placed in an incubator with the water sample to be tested, then it is fed with the fluorescent beads for a set period of time.

(b) The washing process: In order to remove the fluospheres remaining on its outer surface the living organisms is flushed with fresh water according to the description FIG. 5(a).

(c) The fluorescence measurement process: When washed, the living organism is carried through the test section as described on FIG. 5(b), where it is forced to flow perpendicularly to a light source. The fluospheres, contained in its digestive tract, chosen to specifically absorb at the selected laser source wavelength, emit a fluorescence signal, detected by the photodector. During the passage of the individual living organism across the test section, a voltage peak can be detected by the detector, processed and recorded by a processing device such as a computer. For each peak, the peak area corresponds to the number of beads contained in each living organism digestive tract.

(d) By analyzing the series of peaks obtained from a living organisms population, a statistical analysis of the population feeding rate can be made. By comparing the feeding rates of a population after an incubation in a toxic sample versus the feeding rates of a population after incubation in a referenced sample a toxicity assessment can be made. The feeding rate measurements decreases accordingly with the toxicity of the sample.

To practice a preferred embodiment invention, the following process and equipment can be used.

Test organisms: The salt water rotifer, *Brachionus plicatilis*. Rotifer cultures are established in the laboratory using dried rotifer cysts purchased from a commercial supplier (Aqua Farms, Florida). They are raised in the laboratory following established practices (Hoff, F. H. and T. W. Snell, "Plankton Culture", Aquafarms, Inc., pp. 147, 1987.)

The Fluorescent Substance: Polysterene latex micro spheres (0.2 micron diameter) coated with fluorescent dyes (FluoSpheres produced by Molecular Probes Inc., 4849 Pitchford Ave., Eugene., Oreg. 97402). The beads have the following characteristics:

Mean diameter 0.415 µm±7.9%. Particle/ml=5.1$\bigcirc$10$^{11}$. Percent solids 2.05% ($\pm$)0.1. Density at 20 degree Celsius 1.055 g/cm3

Device to assess bead ingestion by the rotifers: This device calculates the number of beads ingested by rotifers exposed to water containing the beads. The estimation of the number of beads ingested is performed by detecting fluorescence of the dye contained in the beads (FIG. 1). The device has the following components:

1. An exposure chamber consisting of glass vials of 15 mm in diameter. Rotifers that were exposed for a known amount of time to a water containing fluospheres and later washed and placed in the exposure chamber in the presence of artificial salt water.

2. A monochromatic source, e.g., a laser or diode laser source and a set of fluospheres.

The light source and the type of fluosphere are chosen to match the source wavelength and the fluosphere dye absorption spectrum. In this example, the light source chosen was a CW Helium Neon laser emitting 1 mJ per second at $\lambda$=632 nm. This translates to a flux of 3.2 e15 photons per second. The laser beam is focused across the test chamber, the size of the focused beam in the middle of the test section in this example was 500 µm.

The spectral characteristic of the fluospheres are also provided by Molecular Probes Inc. For this embodiment, crimson is chosen as a dye. The maximum photon absorption of crimson was measured at 624 nm and the maximum fluorescence emission coefficient was measured to be at 645 nm, and the dye concentration in each polystyrene bead is 14 µmol/g.

3. A set of two filters compatible with the dye fluorescence emission spectra. A 52 mm red 29, dark red low pass filter, manufactured by Tiffen, of Hauppauge, N.Y., is used to block the radiation at a wavelength smaller than 640 nm with a transmission coefficient less than 0.1%. To fully block the laser light and to only record the fluorescence signal, one may use a specific interference filter made by Omega, Inc., and referred to as 670DF27.4. This filter was designed to have the following transmission coefficients T(645±10 nm)= 60% and T=1e-06, everywhere else up to $\lambda$<500 nm.

4. A spherical lens of a 100 mm focal length is used to focus the laser source in the test section. The 500 µm laser beam is imaged onto a pinhole of a photo detector using a 35 mm f 1/3.5 Cannon lens. The collecting lens and pinhole size were chosen to obtain a 250 µm resolution, which corresponds to a typical size of the studied living organism.

5. Imaging equipment: the laser beam is imaged with a 35 mm Cannon f/3.5 lens onto a R 666 photo cathode of a photo multiplier Hamamasu with a quantum efficiency of 1% at 650 nm. In this example the High Voltage was set to be 1200 V. A low pass filter is then placed in front of the photomultiplier photocatode to filter the laser light scattered by the test organisms at $\lambda$=633 nm. The filter transmits the bead fluorescence light at 650 nm. The photo multiplier delivers a 0–5 Volt DC output signal, which is connected on the input of a analog digital conversion board.

6. A 12 bit analog digital converter and a numerical processing and data storage device. In this case we used a CYRDAS 8 converter board (CyberResearch.Inc., P.O. Box 9565, New Haven, Conn. 06535-0565) and a computer. The acquisition bus is a IBM-PC compatible and features a high speed, 12 bit of dynamic range, with a 25 microsecond conversion time, and provides a ±5 volt DC input. The 0–5 Volt on-line signal coming from the detector was sampled at a 50 Hz rate, digitized onto a 12 bit dynamic range, with a precision of 1.2 mV, and then stored for further data processing.

To analyze the fluorescence signal coming on to the detector during the passage through the test section of an individual organism with a digestive tract containing a number of beads, we utilize the following assumptions:

a) The fluorescence is an isotropic process
b) The concentration of bead is homogenous in the animal digestive tract
c) The laser intensity is uniformed across the beam
d) The organism digestive tract is small enough to assume a linear absorption regime According to the diagram shown (FIG. 2), the equation for the voltage signal coming from the photo-detector can be written as follows:

$$S_D(t) = K \otimes \frac{\Omega}{4\pi} \otimes T_F \otimes \qquad (4)$$

$$q_{\mathit{eff}}\left( a \otimes \phi \otimes \frac{N_b}{g} \otimes \epsilon_b \otimes P_L \otimes f(t)) + S_B(t) \right)$$

In this embodiment, the number of beads, the presence of the rotifers in the probe volume and the background intensity are all functions of time.

t=the time, all the data time series will be expressed in function of this variable.

$S_D(t)$=the photon signal imaged onto the photo-multiplier.
K=a calibration constant.

The detector quantum efficiency qeff=0.0 1, for the R 666 photo cathode at λ=645 nm.

$P_L$=the Helium Neon 633 nm laser power. In average a flux of 3.2 1015 photons per seconds.

$S_B(t)$=the background signal detected by detector when no fluorescence is observed.

a=the transmission coefficient of the rotifer at the laser wavelength.

The collection solid angle Ω=0.4 steradian, normalized by 4Π steradian (all space collection).

$N_b$ (t)=the number of fluospheres per unit of length of the probe volume at a given time.

$T_F$=is the transmission coefficient of the set of filters. One innovative aspect of the present invention is the ability to discriminate the fluorescence signal coming from the beads in the digestive tract of the rotifers, from the laser light scattered by the rotifers when they swim through the probe volume. The set of filters chosen is important in this experiment because it has transmission coefficients of TF=0.6 at λ=645 nm (maximum of the crimson fluorescence signal) and a coefficient TF=1e-06 at the laser wavelength smaller than λ=633 nm.

g=the length of the rotifer's digestive tract.

$\epsilon_b$=the absorption coefficient of one fluosphere.

φ=the fluorescence efficiency of a fluosphere.

f(t)=a triangle function, as shown on (FIG. 2), representing the passage of the rotifer across the probe volume; f(t) is artificially set to 1 when the rotifer is in the middle of the probe volume and decreases to zero when is not present in the probe volume. In an intermediary position, f(t) represents the ratio of the rotifer volume which intersects with the laser probe volume.

Equation (4) can be divided in two parts representing the fluorescence signal and the background signal as follows:

$$S_D(t) = S_F(t) + S_B(t) \qquad (5)$$

The signal to noise ratio is determined similarly to the method as described by P. J. Goix, K. R. Leonard, L. Talbot, and J. Y. Chen, "Direct Measurement of Mixture Fraction in Reacting Flow Using Rayleigh Scattering", Experiments in Fluids, Vol. 15, pp. 247–254, 1993. In this case, it is defined by the fluorescence signal recorded when the living organism crosses the probe volume divided by the background fluctuation signal when there is no rotifer with beads present:

$$\text{Signal/Noise} = \frac{\overline{S_D}}{\sqrt{\mathit{var}(S_B)}} \qquad (6)$$

$\overline{S_D}$ = the averaged maximum flourescence signal obtained when the rotifer is swimming through the probe volume.

$\sqrt{\mathit{var}(S_B)}$ = the averaged background fluctuation observed when there are no beads in the rotifer's digestive tract.

To evaluate this ratio, the following experiment has been performed by the Applicant:

Two test chambers (TC1 and TC2) were prepared. Each TC contained 10 rotifer/ml (the concentration of rotifers in each TC was calculated by counting, using a microscope, the number of rotifers in replicated 20 μl droplets). The rotifers in TC1 were suspended in pure artificial salt water. The rotifers in TC2 had been exposed to a latex fluosphere solution for 10 minutes. To accomplish this a 10 μl of the commercial bead preparation was added to 200 ml of artificial salt water in an Erlenmeyer flask (the concentration of beads obtained was 25106 spheres/ml). A heavy suspension of rotifers was added to this chamber. The rotifers were allowed to remain in this suspension for 10 minutes. After 10 minutes the rotifers were removed from the solution by pouring the suspension into a funnel lined with filter paper. The rotifers, retained by the filter paper were rinsed three times with artificial salt water to remove any fluospheres that may have been on their exterior.

Figure 4A:
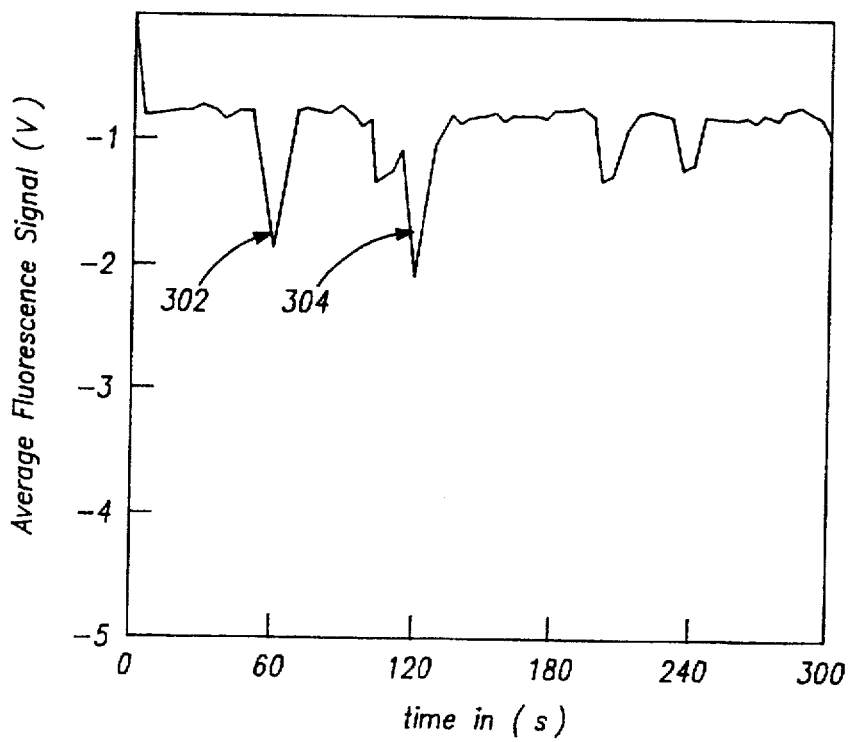
FIG. 4(a) shows a display of the detector output when rotifers cross the probe volume and have ingested crimson fluosphere during 10 minutes prior to the measurement.

FIG. 3 and FIG. 4(a) show typical detector output time series when TC1 and TC2 were successively placed in the dark chamber. On these figures, the detector output in volt is shown at the vertical axis, and the time in seconds on the horizontal axis. Each test chamber was placed in the device in the dark for 300 seconds. The signal coming from the photo-detector was sampled at a 50 Hz frequency, the data digitized with a 12 bit resolution were stored in the memory of a 486 IBM compatible computer.

FIG. 3 represents a signal photo-multiplier output when individual organisms nonexposed to the fluorescent beads are crossing the He-Ne laser beam while flowing through the probe volume. The signal 202 exhibited on (FIG. 3) is very small and lower than −150 mv. The output signal of the photo detector exhibited on (FIG. 3) is flat. Its average is 0.134 volt and the square root of its variance is 0.016 volt. This demonstrates that the signal scattered by the rotifers (without fluorescence beads in their digestive tract) is well filtered by the filter set 12 or 114, as described on (FIG. 1) and (FIG. 2) respectively, and no peak is observed in that case.

FIG. 4(a) represents typical fluorescence peaks 302 and 304. These peaks correspond to the passage of two rotifers crossing the probe section as described on FIG. 3; but, in this case, after being exposed to crimson fluospheres for 10 minutes and washed thoroughly prior to the measurement. In this case, the peak value for 302 is −1.8 volt and −2.1 volt for peak 304. In this case, the signal to noise ratio defined as (6) is 125. In the absence of the rotifer presence, a residual base level of −0.5 volt can also be observed. We attribute this base level to a residual external presence of fluorescence beads after the living organism washing process. We proposed that this base level signal be removed numerically or reduced by a more thorough washing process.

FIG. 4(b) represents a signal peak 306 obtained during the passage of the rotifer across a the laser after being exposed the crimson beads for 20 minutes and subsequently thoroughly washed. FIG. 4(b) shows that when the feeding time is increased up to 20 minutes, the peak intensity increases to −3 volt and the signal to noise ratio can even reach a 200 value. FIG. 4(c) represents a signal peak 310 obtained in similar conditions as for the FIG. 4(b) and (FIG. 4(a), with an exposure time of 45 minutes. In this case, the intensity of the peak 310 is found to be −5 V.

The frequency and the intensity of the fluorescence peaks observed on FIGS. 4(a), (b), (c) are functions of the following parameters:

1. The concentration of living organisms swimming in the test section.
2. The types of living organism and food coating the beads.
3. The size and the concentration of the beads used to monitor the rotifer feeding process.
4. The of variation in sizes of the living organism population to be probed.
5. The bead ingestion time.
6. The trajectories of the rotifers crossing the laser probe volume.

These variables can be controlled by calibrating the population to be tested and controlling the concentration and size of the beads to be used as a biomarker.

For example, one way to count the living organisms and at the same time to control their respective trajectories is to force the living organisms to flow perpendicularly across the laser probe volume. As shown on FIG. 5(a) and FIG. 5(b), a water flow controlled by, but not limited to, a peristaltic pump would force the rotifers to swim perpendicularly across the laser probe. By detecting each fluorescence peak using this method the living organism could be automatically tagged. This method would also alleviate the rotifer trajectory ambiguity problem on the fluorescence peak measurements.

Figure 6:
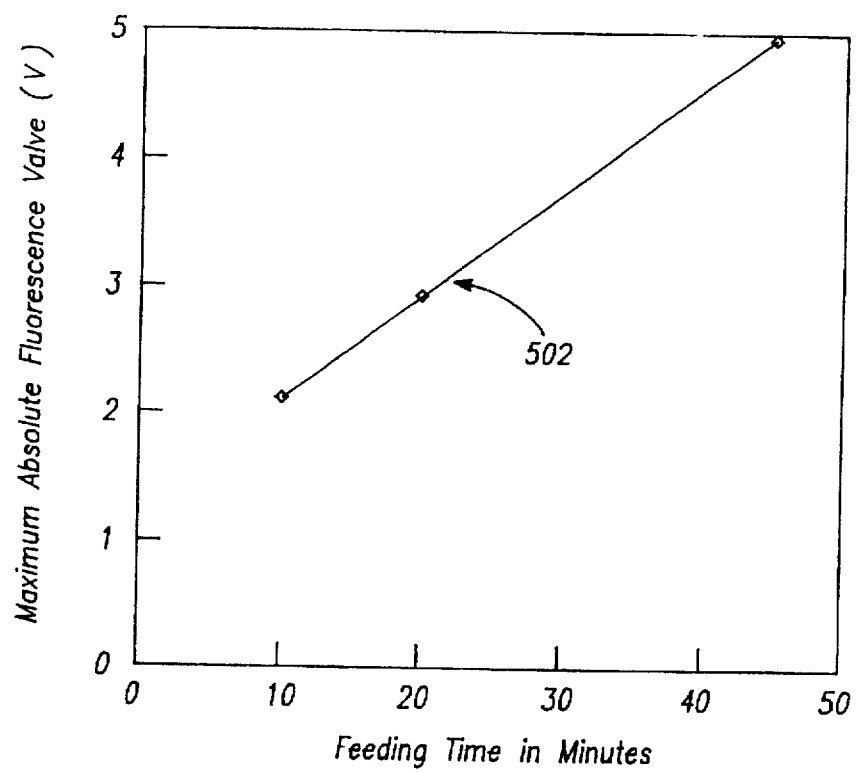
FIG. 6 shows a correspondence table between the detected fluorescence signal and the biomarker exposure time.

To assess the relationship between the living organism feeding rate and the fluorescent experiment, three feeding times were investigated. For these three cases, the size and the concentration were kept constant at 0.46 μm and 25106 sphere/ml respectively. The living organisms chosen to perform this experiment, rotifers in this example, were randomly selected in the three cases from the same original population. The concentration of the rotifers in the three test sections was 40 (±5) rotifers per 10 ml. The rotifers were exposed to the same fluosphere bead water sample for 10 minutes, 20 minutes, and 45 minutes, respectively. On (FIG. 6) the fluorescence maximum peak values in rotifers on the vertical axis, obtained on (FIGS. 4.(a), (b), (c) and respectively labeled as 306, 308, 310, are plotted versus the rotifer feeding time in minutes on the horizontal axis. A linear interpolation of this plot 502 is presented. The linear interpolation 502 can be represented by y=at+b where y is the maximum peak signal, and t is the incubation time. In this case a=82 milivolt and b=1.1 volt.

The relationship of the peak intensity 306, 308, and 310 with the incubation time, in this case, is found to be monotone and linear; therefore the fluorescence output voltage can be calibrated as a function of the rotifer feeding rate without ambiguity. The calibration table will enable the conversion of the fluorescence signal into a feeding rate data.

Figure 7:
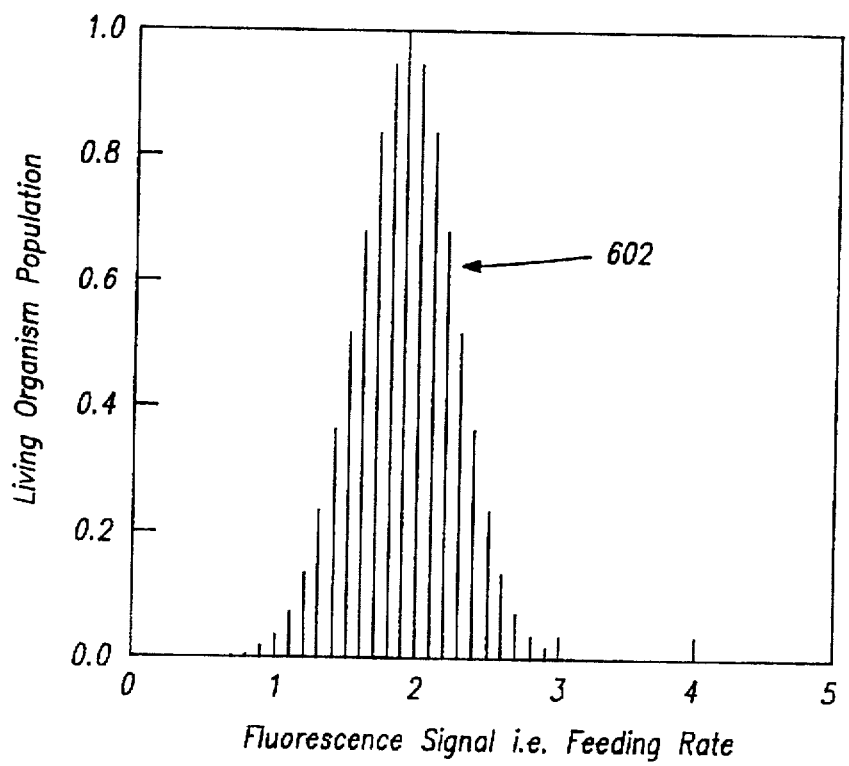
FIG. 7 shows a simulated Gaussian distribution of rotifer feeding rate response in a non toxic environment.
Figure 8:
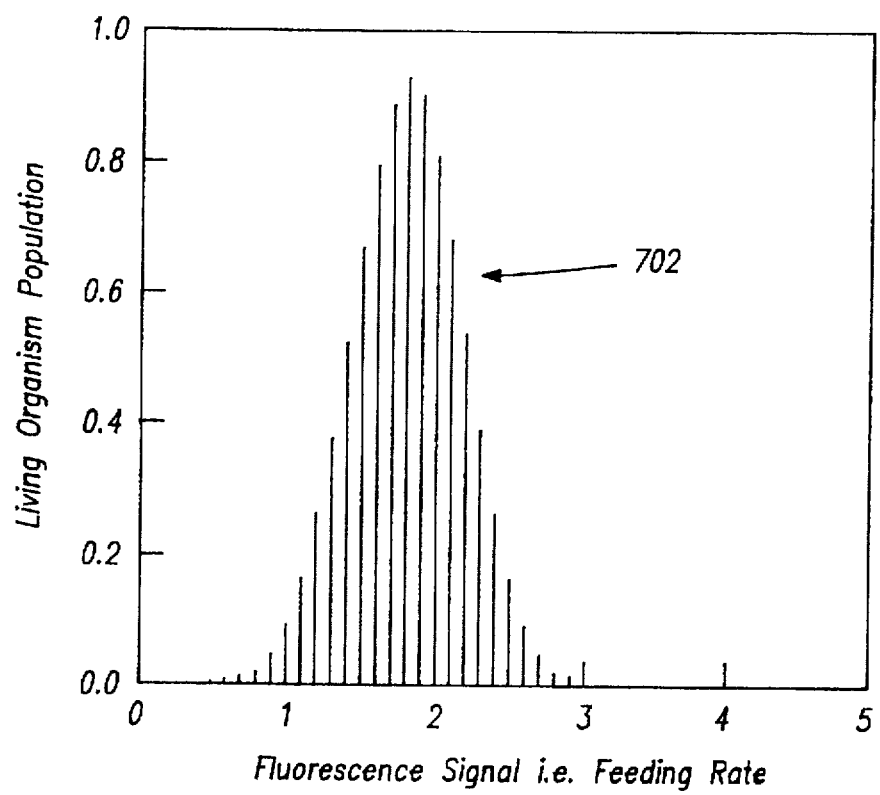
FIG. 8 shows a simulated Gaussian distribution of rotifer feeding rate response in a toxic environment.

According to Snell et al., ("Biomarkers for Managing Water Resources", University of Georgia, May 1993), the presence of a toxicant in a water sample decreases the rotifer feeding rate over a wide range of chemicals; therefore, the rotifer response when the rotifer is exposed to a toxic water sample using our method is expected to be different from the rotifer response when it is exposed to a non-toxic water sample, everything else being equal. FIG. 7 and FIG. 8 represent a simulation of two Gaussian distribution of individual live animal feeding rate measurements by the fluorescence technique described earlier. For both figures, the number of living organisms, normalized by the number of living organisms at the peak distribution, is plotted on the vertical axis versus the fluorescence signal corresponding to the number of ingested beads, in volts on the horizontal axis. On FIG. 7 the feeding rate distribution 602 has an averaged value of 2 volt and a root mean square (rms) value of 0.5 V. For the distribution 702 depicted on FIG. 8 a decrease of the feeding rate due toxicant exposure was assumed to affect 50% of the population. By varying two typical fluorescence peak exponential distributions, on FIG. 7 when the rotifers were exposed to a referenced non-toxic water sample, and on FIG. 8 when the rotifers were exposed to a water sample to be tested, a toxicity assessment of the test sample can be made.

In particular, if the test sample is toxic, a shift toward smaller fluorescence value is expected, as shown on FIG. 8. In this case, we assumed that the rotifer feeding rate affected by a hypothetical toxic sample was reduced by 10%, causing a reduction of the fluorescence signal by 30%. In this example only 50% of the population exposed has been affected.

According to the EPA (EPA. loc. cit. p. 5, 1985), a safe concentration of toxicant can be defined in seven different ways: the Non- Observed-Effect-Concentration, (NOEC); the Lowest-Observed Effect Concentration (LOEC); the Maximum Acceptable Toxicant Concentration (MATC); the Chronic Value (ChV); the Effective Concentration (EC) (this concentration is based on a toxicant concentration causing an observable adverse effect ( such as death, immobilization, incapacitation, reduced fecundity, or reduced growth); the Lethal Concentration (LC) (based on a death rate only); and, finally, the Inhibition Concentration (IC) (based on a reduction in a non-quantal biological measurement such as fecundity or growth).

These concentration measurements are based on the choice of an appropriate living organisms to be tested and a tool to measure an observable effect over a full or partial life cycle. For example, the EC50 is the estimated concentration of toxicant that would cause an observable effect, say change in feeding rate, over 50% on the population of the living organism considered for the test.

This device will provide a genuine way to measure these concentrations according to EPA guidelines.

The benefits of our device and methodology are many and include, without limitation, the following:

1. Easy to use on site

The laser, the computer, and the detector can be miniaturized and battery powered. Our device can be used for in-site water toxicity assessment.

2. Automatic

Current acute and chronic toxicity procedures based on lethality, growth and reproduction, are labor intensive, expensive, and take a long time. (Gary M. Rand and Sam Petrocelli., "Fundamentals of Aquatic Toxicology, Methods and Applications", Hemisphere Pub. Corp. 1985). Our method is automatic; it tags the living organisms passing through the probe volume and measures their feeding rate by recording a fluorescence signal on a computer memory. The toxicity level is then evaluated by data processing.

3. Sensitive and reliable

Most of the current methods to assess toxicity rely heavily on statistics. (EPA. loc. cit. p. 5, 1985). Toxicity, in general, is assessed when a statistical effect on a living organism population can be measured. Since biological differences can be observed in the reproduction, growth, and feeding functions from one living organism to another, the higher the number of samples taken, the smaller the variation of the distributions will be. In providing an automatic tool, here a fluorescence tool, to assess a biological effect, say feeding rate, on a specific living organism, a rotifer, a larger number of sample can be obtained per test. Therefore, a better estimate of the living organism population can be made and a small variation will result. Therefore, smaller departures from the distribution of reference, the non-toxic sample containing healthy rotifers, can be observed.

This method is also sensitive and precise because it is and almost free of any electronic noise. Since the fluorescence signal is detected with a very large signal to noise ratio, the feeding rate measurement can be measured with precision.

4. Applicable to a wide range of conditions

The present invention can be used to measure a wide range small organisms that ingest particles in water, and are transparent over a wide range of light wavelength. Rotifers, Daphnia, and Ceriodaphnia are particularly well suited for our method because they have these characteristics.

5. Advantage of using the laser source

As opposed to the existing methods using radiation sources emitting around the 480 nm range for the epifluorescent microscope techniques and in the UV range for the microtox test and the technique proposed by Hayse, K. R. (U.S. Pat. No. 5,094,944, loc. cit. 1992), our method allows to operate at a wide range of wavelengths, from the near Infrared to the UV range. We have selected a laser emitting at 632 nm and a set of crimson fluospheres absorbing efficiently at this wavelength, in this example, to show that this method could be applied using a diode laser operating at similar wavelength and light power output and offering the potential of portability and energy autonomy inherent to the diode laser devices.

6. Potential for measuring other biological functions

Because this technique can be used over a wide range of selected wavelengths, it can be used to monitor other biological functions than the feeding rate function, such as the reproduction rate function. Similarly by tagging the eggs of organisms such as rotifers or daphnia with a selected dye or by selecting a laser light source according to the egg spectral absorption characteristics, the number of eggs transported by such organisms could be monitored by the same technique. Because the laser has a narrow wavelength emission band, typically a few nanometers, it offers selectivity in absorption mediums; hence, at specific wavelengths only the reproductive part of the organism could be monitored for example.

While the present invention has been described in connection with certain preferred embodiments, the present invention is not limited to such embodiments. Rather, the scope of the invention is defined by the claims.

What is claimed is:

1. A device for detecting a fluorescent substance tagged to a living microorganism comprising:

a flow carrier system for transporting the microorganism past a selected location;

a source of electromagnetic radiation for irradiating the substance tagged to the microorganism; and a detection system for measuring fluorescent light emitted from the substance at the selected location.

2. The device of claim 1, wherein said source of radiation comprises a source of light.

3. The device of claim 2, wherein said source of light comprises a laser.

4. The device of claim 1, wherein a plurality of microorganisms are individually transported past the selected location at a substantially uniform velocity.

5. The device of claim 1, wherein the living microorganism is an animal.

6. The device of claim 5, wherein the animal is a rotifer.

7. The device of claim 1, wherein the substance tagged to the microorganism is ingested by the microorganism.

8. The device of claim 1, further comprising a means for exposing the microorganism to a toxic substance.

9. The device of claim 8, wherein the fluorescent substance is ingested by the microorganism, and exposure of the microorganism to the toxic substance affects the rate of ingestion of the fluorescent substance by the microorganism.

10. The device of claim 9, further comprising means for calculating the ingestion rate as a function of the amount of fluorescent light emitted from the fluorescent substance at the selected location.

11. A device for assessing the amount of a fluorescent substance associated with an animal, comprising:

a flow carrier for transporting the animal to a selected location;

a source of electromagnetic radiation for irradiating the substance associated with the animal; and a detector for measuring light emitted from the substance at the selected location.

12. The device of claim 11, further comprising means for exposing the animal to a toxic substance, the toxic substance affecting a selected biological function of the animal.

13. The device of claim 12, further comprising means for obtaining information relating to said selected biological function from the light emitted from the substance at the selected location.

14. The device of claim 1, wherein the flow carrier automatically orients the microorganism so that the amount of the fluorescent substance can be assessed.

* * * * *

UNITED STATES PATENT AND TRADEMARK OFFICE
CERTIFICATE OF CORRECTION

PATENT NO. : 5,798,222
DATED : August 25, 1998
INVENTOR(S) : Philippe Goix

It is certified that error appears in the above-identified patent and that said Letters Patent is hereby corrected as shown below:

On the title page, Item [54], and Column 1, line 1-2, should be
-- APPARATUS AND METHOD FOR MONITORING SUBSTANCES IN ORGANISMS--

Signed and Sealed this

Twenty-seventh Day of July, 1999

Attest:

Q. TODD DICKINSON

*Attesting Officer*  *Acting Commissioner of Patents and Trademarks*